United States Patent
Park

(10) Patent No.: US 10,383,592 B2
(45) Date of Patent: Aug. 20, 2019

(54) APPARATUS AND METHOD FOR AIDING IMAGING DIAGNOSIS

(71) Applicant: Samsung Electronics Co., Ltd., Suwon-si (KR)

(72) Inventor: Jin Man Park, Yongin-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 857 days.

(21) Appl. No.: 14/808,426

(22) Filed: Jul. 24, 2015

(65) Prior Publication Data
US 2016/0022238 A1   Jan. 28, 2016

(30) Foreign Application Priority Data
Jul. 25, 2014   (KR) .................. 10-2014-0094877

(51) Int. Cl.
| | | |
|---|---|---|
| A61B 6/00 | (2006.01) | |
| A61B 5/055 | (2006.01) | |
| A61B 8/08 | (2006.01) | |
| A61B 5/00 | (2006.01) | |
| G06T 7/00 | (2017.01) | |
| G06T 7/64 | (2017.01) | |
| A61B 6/03 | (2006.01) | |
| A61B 8/00 | (2006.01) | |

(52) U.S. Cl.
CPC .......... *A61B 6/5217* (2013.01); *A61B 5/055* (2013.01); *A61B 5/7264* (2013.01); *A61B 5/748* (2013.01); *A61B 8/5223* (2013.01); *G06T 7/0012* (2013.01); *G06T 7/64* (2017.01); *A61B 6/032* (2013.01); *A61B 6/469* (2013.01); *A61B 6/486* (2013.01); *A61B 8/085* (2013.01); *A61B 8/469* (2013.01); *G06T 2207/10072* (2013.01); *G06T 2207/20081* (2013.01)

(58) Field of Classification Search
CPC combination set(s) only.
See application file for complete search history.

(56) References Cited

U.S. PATENT DOCUMENTS

| | | | | |
|---|---|---|---|---|
| 7,054,473 | B1 * | 5/2006 | Roehrig | G06F 19/321 |
| | | | | 382/128 |
| 2002/0097902 | A1 | 6/2002 | Roehrig et al. | |
| 2003/0161513 | A1 * | 8/2003 | Drukker | G06T 7/0012 |
| | | | | 382/128 |
| 2006/0173292 | A1 * | 8/2006 | Baba | A61B 8/469 |
| | | | | 600/425 |

(Continued)

FOREIGN PATENT DOCUMENTS

| | | |
|---|---|---|
| JP | H0683880 A | 3/1994 |
| JP | 2014-059892 A | 4/2014 |

(Continued)

*Primary Examiner* — James M Kish
(74) *Attorney, Agent, or Firm* — Jefferson IP Law, LLP

(57) ABSTRACT

An apparatus and method for aiding imaging diagnosis is provided. The imaging diagnosis aiding apparatus includes: an extractor configured to extract at least one medical image feature from medical images, a diagnosis component configured to determine whether a lesion is malignant or benign based on the at least one extracted medical image feature, and a display configured to display supplementary diagnosis information in response to a reliability of the determination being above a predetermined threshold.

19 Claims, 5 Drawing Sheets

(56) References Cited

U.S. PATENT DOCUMENTS

| | | | |
|---|---|---|---|
| 2006/0210133 A1* | 9/2006 | Krishnan | G06F 19/00 382/128 |
| 2006/0274928 A1* | 12/2006 | Collins | A61B 6/00 382/132 |
| 2011/0123073 A1* | 5/2011 | Gustafson | G06F 19/321 382/128 |
| 2012/0166211 A1 | 6/2012 | Park et al. | |
| 2014/0033126 A1 | 6/2014 | Kreeger et al. | |

FOREIGN PATENT DOCUMENTS

| | | | |
|---|---|---|---|
| KR | 20070081803 A | * | 8/2007 |
| KR | 10-2012-0072961 A | | 7/2012 |

\* cited by examiner

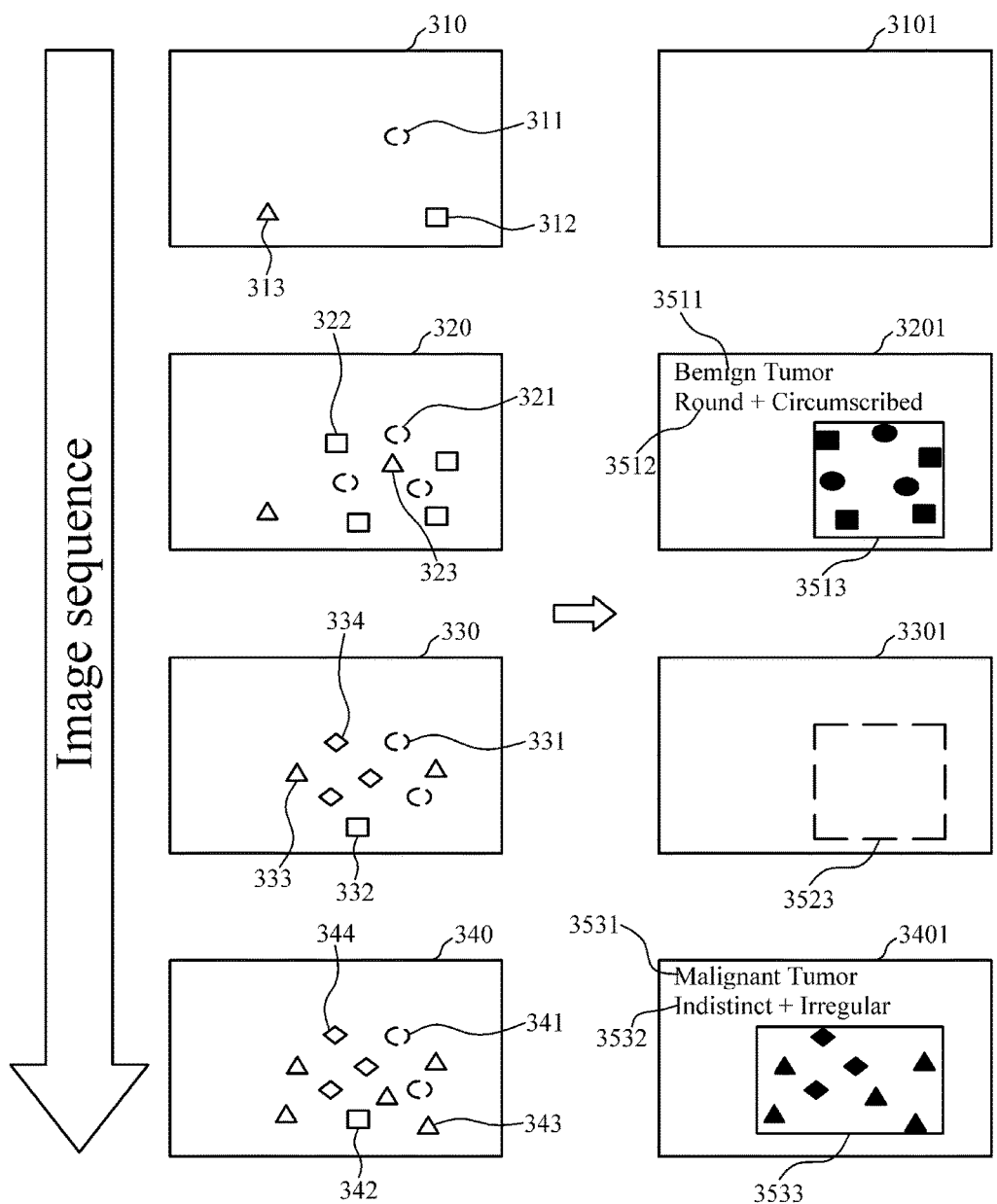

APPARATUS AND METHOD FOR AIDING IMAGING DIAGNOSIS

CROSS-REFERENCE TO RELATED APPLICATION(S)

This application claims priority from Korean Patent Application No. 10-2014-0094877, filed on Jul. 25, 2014, in the Korean Intellectual Property Office, the entire disclosure of which is incorporated herein by reference for all purposes.

BACKGROUND

1. Field

The following description relates to an apparatus and method for aiding imaging diagnosis.

2. Description of Related Art

Doctors may diagnose diseases with the aid of imaging diagnosis by using an ultrasound probe to analyze a consecutive sequence of medical images acquired in real time or a previously acquired sequence of Two-Dimensional (2D) or Three-Dimensional (3D) medical images.

A Computer-Aided Diagnosis (CAD) system may analyze a single image to extract suspected malignant regions, and may mark the extracted regions by using a cross, box, tumor segmentation, or other similar patterns. In the case of using the CAD system to analyze a sequence of medical images, doctors may be visually confused when analyzing the sequence of medical images since the CAD system may diagnose benignancy or malignancy and may mark suspected regions for each image frame. Further, a false alarm of the CAD system may disrupt doctors' diagnoses.

Accordingly, there is provided a CAD system that may aid in imaging diagnosis with minimal confusion to the doctor.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In a general aspect, there is provided an imaging diagnosis aiding apparatus, including an extractor configured to extract at least one medical image feature from medical images, a diagnosis component configured to determine whether a lesion is malignant or benign based on the at least one extracted medical image feature, and a display configured to display supplementary diagnosis information in response to a reliability of the determination being above a predetermined threshold.

The diagnosis component may determine whether the lesion is malignant or benign based on a combination of one or more of the at least one extracted medical image feature.

The diagnosis component may determine whether the lesion is malignant or benign by comparing the at least one extracted medical image with a pre-stored diagnosis model.

The supplementary diagnosis information may include at least one of: details about medical image features that lead to the determination, an image location that includes the medical image features that lead to the determination, or a region of interest upon a determination of whether the lesion is malignant or benign.

The region of interest is a region that may include medical image features that lead to the determination, and may include regions having a coherence of each pixel that is above a predetermined threshold.

The display may be configured to display the region of interest in the medical image and in an image frame subsequent to the medical image.

The display may be configured to display the region of interest with a dotted line in the subsequent image frame.

The medical image may include a Computed Radiography (CR) image, a Computed Tomography (CT) image, an ultrasonic image, and a Magnetic Resonance Image (MRI).

The imaging diagnosis aiding apparatus may further include a preprocessor configured to preprocess the medical image by performing at least one of normalization, channel separation, and scaling.

In another aspect, there is provided a method of aiding imaging diagnosis, the method including extracting at least one medical image feature from a medical image, determining whether a lesion is malignant or benign based on the at least one extracted medical image feature, and displaying supplementary diagnosis information in response to a reliability of the determination being above a predetermined threshold.

The determination may include determining whether the lesion is malignant or benign based on a combination of one or more of the at least one extracted medical image feature.

The determination may include determining whether the lesion is malignant or benign by comparing the at least one extracted medical image with a pre-stored diagnosis model.

The supplementary diagnosis information may include at least one of: details about medical image features that lead to the determination, an image location that may include the medical image features that lead to the determination, or a region of interest upon a determination of whether the lesion is malignant or benign.

The region of interest is a region that may include medical image features that lead to the determination, and may include regions having a coherence of each pixel that is above a predetermined threshold.

The displaying may include displaying the region of interest in the medical image, and displaying the region of interest in an image frame subsequent to the medical image.

The displaying of the region of interest in an image frame subsequent to the medical image may include displaying the region of interest with a dotted line in the subsequent image frame.

The medical image may include a Computed Radiography (CR) image, a Computed Tomography (CT) image, an ultrasonic image, and a Magnetic Resonance Image (MRI).

The method of aiding imaging diagnosis may further include preprocessing the medical image by performing at least one of normalization, channel separation, and scaling.

There is also provided a non-transitory computer-readable medium storing program instructions for controlling a processor to perform the method of aiding imaging diagnosis.

Still further, there is provided an imaging diagnosis aiding apparatus, including a diagnosis component configured to determine a lesion is a malignant lesion or a benign lesion based on the at least one extracted medical image feature extracted from received medical images, and a display configured to display supplementary diagnosis information in response to a reliability of the determination being above a predetermined threshold.

The diagnosis component may determine whether the lesion is malignant or benign based on a combination of one or more of the at least one extracted medical image feature.

The supplementary diagnosis information may include details about a combination of the medical image features that lead to the determination that a lesion is a malignant tumor, image locations that include the image feature having a round shape and the image feature having a circumscribed margin, and a region of interest.

The imaging diagnosis aiding apparatus may further include an input component configured to receive input of medical images or receive input of image frames that constitute a sequence of successively captured images.

Other features and aspects will be apparent from the following detailed description, the drawings, and the claims.

BRIEF DESCRIPTION OF THE DRAWINGS

FIG. 3 is a block diagram illustrating an aspect of using an apparatus for aiding imaging diagnosis in real-time ultrasound examination of a breast cancer.

Figure 1:
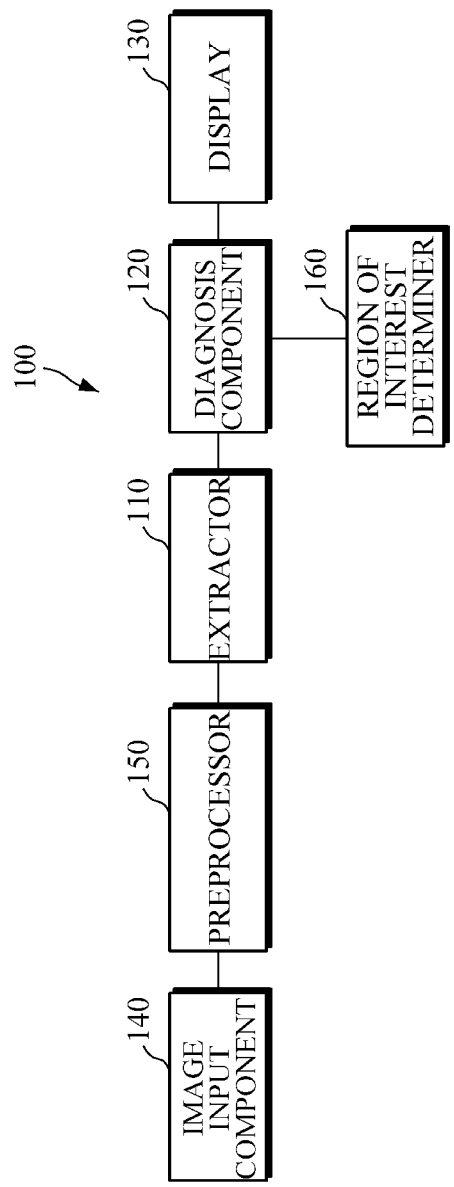
FIG. 1 is a block diagram illustrating an aspect of an apparatus for aiding imaging diagnosis.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. However, after an understanding of the present disclosure, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that may be well known to one of ordinary skill in the art may be omitted for increased clarity and conciseness.

The features described herein may be embodied in different forms, and are not to be construed as being limited to the examples described.

FIG. 1 is a block diagram illustrating an aspect of an apparatus for aiding imaging diagnosis.

Referring to FIG. 1, the apparatus 100 for aiding imaging diagnosis (hereinafter referred to as "imaging diagnosis aiding apparatus") includes an extractor 110, a diagnosis component 120, and a display 130, an image input component 140, a preprocessor 150. And a Region of Interest (RIO) determiner 160.

The extractor 110 may extract medical image features from medical images, in which the medical image may be any one of various medical images, including a Computed Radiography (CR) image, a Computed Tomography (CT) image, an ultrasonic image, a Magnetic Resonance Image (MRI), and similar alternatives. Further, the medical image may be an image frame constituting a sequence of successively captured images.

Specifically, the extractor 110 may process images to extract a region suspected to have a lesion from medical images, and may extract features of medical images by using pixel information of contours of the extracted region, regions adjacent to the contours, or regions within the contours. In this context, the lesion may refer to a region in an organ or tissue that has suffered damage through injury or disease, such as a wound, ulcer, abscess, tumor, etc.

The features of the medical images refer to medically meaningful features that include visual pattern information of cell tissues that may be used to determine whether a lesion is a non-cancerous benign lesion or a cancerous malignant lesion.

Malignant lesions or tumors generally have cell tissues of which shapes are irregular and their margins are indistinct, whereas benign lesions or tumors have cell tissues of which shapes are round and their margins are circumscribed. Accordingly, the shapes, sizes, margins, or similar features of cell tissues may be used as criteria to determine benignancy of malignancy of tumors such that the features of certain areas in medical images may be classified according to characteristics of the features, such as shapes, sizes, margins, or the like. The shapes, sizes, and margins are described as examples of classification characteristics of features, but the characteristics are not limited thereto, and may include various characteristic features, such as echo pattern, orientation, boundary, texture, intensity, etc., which may be used to determine whether a lesion is malignant or benign.

Classification characteristics, medical image features classified into each classification characteristic, and criteria to determine each medical image feature may be predetermined by a user.

In an exemplary aspect, the medical image features may be lesion features classified according to a Breast Imaging Reporting and Data System Lexicon (BI-RADS), but are not limited thereto, and may be determined in consideration of features according to the types of medical images (e.g., MRI, ultrasonic images, etc.) as well as the captured portion (e.g., breast, thyroid, etc.).

The extractor 110 may be implemented by various algorithms for image recognition, feature extraction, and machine learning, such as Deformable Part Model (DPM), Auto Encoder, and similar alternatives.

The diagnosis component 120 may diagnose lesions based on medical image features extracted by the extractor 110.

Specifically, the diagnosis component 120 may determine whether a lesion is benign or malignant by comparing the extracted medical image features with a pre-stored diagnosis model. A diagnosis model may be generated by machine learning using medical image features extracted from various pre-collected diagnosis images, and the generated diagnosis model may be stored in a database located inside or outside the diagnosis component 120. The diagnosis model may include combinations of medical image features as wells as diagnosis results according to each combination of medical image features.

Diagnosis results of the diagnosis component 120 may include determination results on whether lesions are benign or malignant, as well as accuracy or reliability of the determinations.

Machine learning algorithms may include artificial neural network, decision tree, Genetic Algorithm (GA), Genetic Programming (GP), Gaussian Process Regression (GPR), Linear Discriminant Analysis (LDA), K-Nearest Neighbor (K-NN), perceptron, radial basis function network, Support Vector Machine (SVM), and similar alternatives.

The display 130 may display supplemental diagnosis information in cases where reliability of a determination is above a predetermined threshold.

The supplemental diagnosis information is information that may be used to aid diagnosis of medical images, and may include information on medical image features that lead to determinations of the diagnosis component 120, such as positions of the medical image features in medical images, regions of interests, as well as other types of information which may aid in the determinations of the diagnosis component 120.

In this case, a Region of Interest (ROI) may be determined based on medical image features that lead to a determination of whether a region is benign or malignant. For example, the ROI may be a region having a medical image feature that leads to determination whether a region is benign or malignant, and may be configured to include regions in which a coherence of each pixel is above a predetermined threshold. To this end, the imaging diagnosis aiding apparatus 100 may further include a ROI determiner 160 that determines the ROI.

In an exemplary aspect, the display 130 may enable the ROI included in a medical image to be displayed in a subsequent frame image so that the ROI may be maintained. That is, the display 130 may enable the ROI, which has been determined and displayed in a previous frame image, to be displayed in the subsequent frame image. In this case, when displaying the ROI, which has been determined and displayed in the previous frame image, in the subsequent frame image, the ROI may be displayed by any method, in which the ROI may be shown with a dotted line or in a specific color, as long as the method enables recognition of the ROI.

In another exemplary aspect, the imaging diagnosis aiding apparatus 100 may further include an image input component 140 and a preprocessor 150.

The image input component 140 may receive an input of medical images. As described above, medical images may be any one of various medical images, including a Computed Radiography (CR) image, a Computed Tomography (CT) image, an ultrasonic image, a Magnetic Resonance Image (MRI), and similar alternatives. Further, the medical image may be an image frame constituting a sequence of successively captured images.

That is, the image input component 140 may sequentially receive input of image frames that constitute a sequence of successively captured images.

The preprocessor 150 may preprocess images in order to easily extract medical image features from medical images. For example, the preprocessor 150 may perform normalization, channel separation, scaling, and similar techniques to medical images.

Hereinafter, supplementary diagnosis information displayed by the imaging diagnosis aiding apparatus 100 will be described in detail with reference to FIGS. 2A and 2B.

Figure 2A:
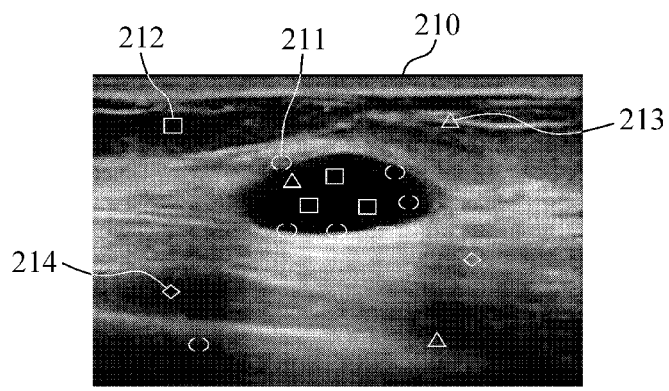
FIG. 2A is a diagram illustrating features of medical images extracted from the medical images.
Figure 2B:
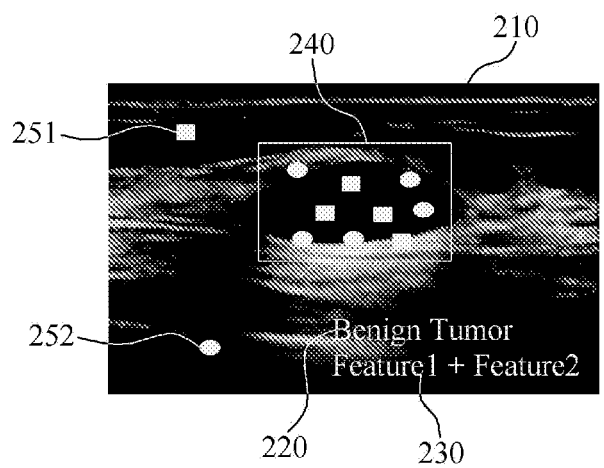
FIG. 2B is a diagram illustrating an aspect of displaying supplementary diagnosis information.

FIGS. 2A and 2B are diagrams explaining a process of displaying supplementary diagnosis information. FIG. 2A is a diagram illustrating features of medical images extracted from the medical images. FIG. 2B is a diagram illustrating an aspect of displaying supplementary diagnosis information, in which a threshold of reliability for displaying supplementary diagnosis information may configured to be at 70%. Medical image feature 1 211 and medical image feature 2 212 are medical image features related to benign tumors. Medical image feature 3 213 and medical image feature 4 214 are medical image features related to malignant tumors.

As noted above, the imaging diagnosis aiding apparatus 100 extracts medical image features from medical images. For example, as illustrated in FIG. 2A, the extractor 110 may extract the medical image feature 1 211, the medical image feature 2 212, the medical image feature 2 213, and the medical image feature 4 214 from a medical image 210.

The imaging diagnosis aiding apparatus 100 determines whether a lesion is benign or malignant based on the extracted medical image features 211 to 214. For example, the diagnosis component 120 may determine whether a lesion is benign or malignant by comparing various medical image features 211 to 214 extracted from the medical image 210 to a pre-stored diagnosis model.

As illustrated in FIG. 2A, the medical image feature 1 211 and the medical image feature 2 212, which are related to benign tumors, are detected in six areas and in five areas respectively, while the medical image feature 3 213 and the medical image feature 4 214, which are related to malignant tumors, are detected in three areas and in two areas respectively. Therefore, the medical image features 212 and 212 related to benign tumors have the numerical preponderance over the medical image features 213 and 214 related to malignant tumors. Based on the determination, the diagnosis component 120 determines that a lesion is a benign tumor with a reliability of 90%.

As the reliability of determination is above a predetermined threshold of 70%, the imaging diagnosis aiding apparatus 100 displays supplementary diagnosis information on display 130 which includes a result of determination, medical image features that lead to the determination, an image position that shows the medical image features, and the ROI.

As illustrated in FIG. 2B, the display 130 displays a determination result 220 that a lesion is a benign tumor, details 230 about medical image features that lead to the determination, an image position of medical image features 211 and 212 that lead to the determination, and a ROI 240.

The ROI 240 is a region that includes the medical image features 211 and 212 that lead to the determination, and may be configured to include regions in which a coherence of each pixel is above a predetermined threshold.

The details 230 about medical image features that lead to the determination that a lesion is a benign tumor may be indicated using terms that represent the medical image features, and may be displayed along with various explanations associated with the medical image features. Further, the result 220 of determination and the details 230 about medical image features may be displayed in a pop-up window as long as it does not hinder observing medical images. The result 220 of determination and the details 230 may also be displayed in a window separately from a window where medical images are displayed. However, the method of displaying of the result 220 of determination and the details 230 about medical image features is not limited thereto, and the result 220 of determination and the details 230 about medical image features may be displayed by various methods as long as the method does not hinder observing medical images.

Further, as illustrated in FIG. 2B, as a method of displaying image locations that include the medical image features 211 and 212 that lead to the determination, a region or a pixel that includes each medical image feature may be displayed using a square, a circle, or a similar pattern, but the method is not limited thereto. Furthermore, various methods may be used to enable recognition of medical image features, including a method of representing a region or a pixel that includes each medical image feature by using different colors to differentiate medical image features.

In an exemplary aspect, as illustrated in FIG. 2B, all the image locations of medical image features that lead to diagnosis may be displayed, or otherwise, only the image locations of the medical image features that are included in the ROI may be displayed. That is, features 251 and 252 in FIG. 2B that are positioned out of the ROI 240 may not be displayed.

FIG. 3 is a block diagram illustrating an aspect of using an apparatus for aiding imaging diagnosis during real-time ultrasound examination of a breast cancer. The left image is a medical image input to an imaging diagnosis aiding apparatus, and the right image is a screen that displays supplementary diagnosis information for each input medical image.

Medical images input to the imaging diagnosis aiding apparatus may be a ultrasound image acquired in real time by an ultrasound probe, in which medical images may constitute a consecutive sequence of images. Further, medical image features are lesion features classified according to the BI-RADS lexicon. Furthermore, a threshold of reliability for displaying supplementary diagnosis information may be configured at 70%.

Round shapes 311, 321, 331 and 341 and circumscribed margins 312, 322, 332 and 342 are medical image features that are associated with benign tumors, and irregular shapes 313, 323, 333 and 343 and indistinct margins 334 and 344 are medical image features that are associated with malignant tumors.

Referring to FIG. 3, once the medical image 1 310 is first input to the imaging diagnosis aiding apparatus 100, the imaging diagnosis aiding apparatus 100 may analyze the medical image 1 310 to extract an image feature 311 having a round shape, the image feature 312 having a circumscribed margin, and the image feature 313 having an irregular shape, such that each of the medical image features 311 to 313 may be extracted in one area. Based on the extracted medical image features 311 to 313, the imaging diagnosis aiding apparatus 100 may perform diagnosis and may determine that a lesion is a normal tissue. If no malignant tumor or benign tumor is detected, supplementary diagnosis information is not displayed on a screen 3101.

Subsequently, once the medical image 2 320 is input to the imaging diagnosis aiding apparatus 100, the imaging diagnosis aiding apparatus 100 may analyze the image feature 321 having a round shape, the image feature 322 having a circumscribed margin, and the image feature 323 having an irregular shape, which are extracted in three areas, four areas, and two areas, respectively. Based on the extracted medical image features 321 to 323, the imaging diagnosis aiding apparatus 100 may perform diagnosis and may determine that a lesion is a benign tumor with a reliability of 75%. Since a lesion is determined as a benign tumor, and reliability is above a predetermined threshold of 70%, a determination result 3511 may indicate that a lesion is a malignant tumor. In addition, details 3512 about a combination of the medical image features 321 and 322 that lead to the determination that a lesion is a malignant tumor, image locations that include the image feature 321 having a round shape and the image feature 322 having a circumscribed margin, and a ROI 3513 are also displayed.

Additionally, once the medical image 3 330 is input to the imaging diagnosis aiding apparatus 100, the imaging diagnosis aiding apparatus 100 may analyze the medical image 3 330 to extract the image feature 331 having a round shape, the image feature 332 having a circumscribed margin, the image feature 333 having an irregular shape, and the image feature 334 having an indistinct margin, which are extracted in two areas, one area, two areas, and three areas, respectively. Based on the medical image features 331 to 334, the imaging diagnosis aiding apparatus 100 may perform diagnosis and may determine that a lesion is a malignant tumor with a reliability of 60%. Although a determination is made that a lesion is a malignant tumor, supplementary diagnosis information is not displayed on a screen 3301 since the reliability is not beyond a predetermined threshold of 70%. However, the ROI 3513, which has been determined in the medical image 2 320 that is a previous frame image and displayed on the screen 3201, is displayed on the screen 3301 of the medical image 3 330 with a dotted line 3523.

Thereafter, once the medical image 4 340 is input to the imaging diagnosis aiding apparatus 100, the imaging diagnosis aiding apparatus 100 may analyze the medical image 4 340 to extract the image feature 341 having a round shape, the image feature 342 having a circumscribed margin, the image feature 343 having an irregular shape, and the image feature 344 having an indistinct margin, which are extracted in two areas, one area, five areas, and three areas, respectively. Based on the extracted medical image features 341 to 344, the imaging diagnosis aiding apparatus 100 may perform diagnosis and may determine a lesion to be a malignant tumor with a reliability of 80%. As a lesion is determined to be a malignant tumor, and the reliability is above a predetermined threshold of 70%, a result 3531 of the determination that a lesion is a malignant tumor, details 3532 about a combination of the medical image features 343 and 344 that lead to the determination that a lesion is a malignant tumor, the image feature 343 having an irregular shape, the image feature 344 having an indistinct margin, and a region of interest 3533 are displayed on a screen 3401.

Although not described herein, the region of interest 3533 displayed on the screen 3401 of the medical image 4 340 may be displayed with a dotted line on a screen of a subsequent frame image.

Figure 4:
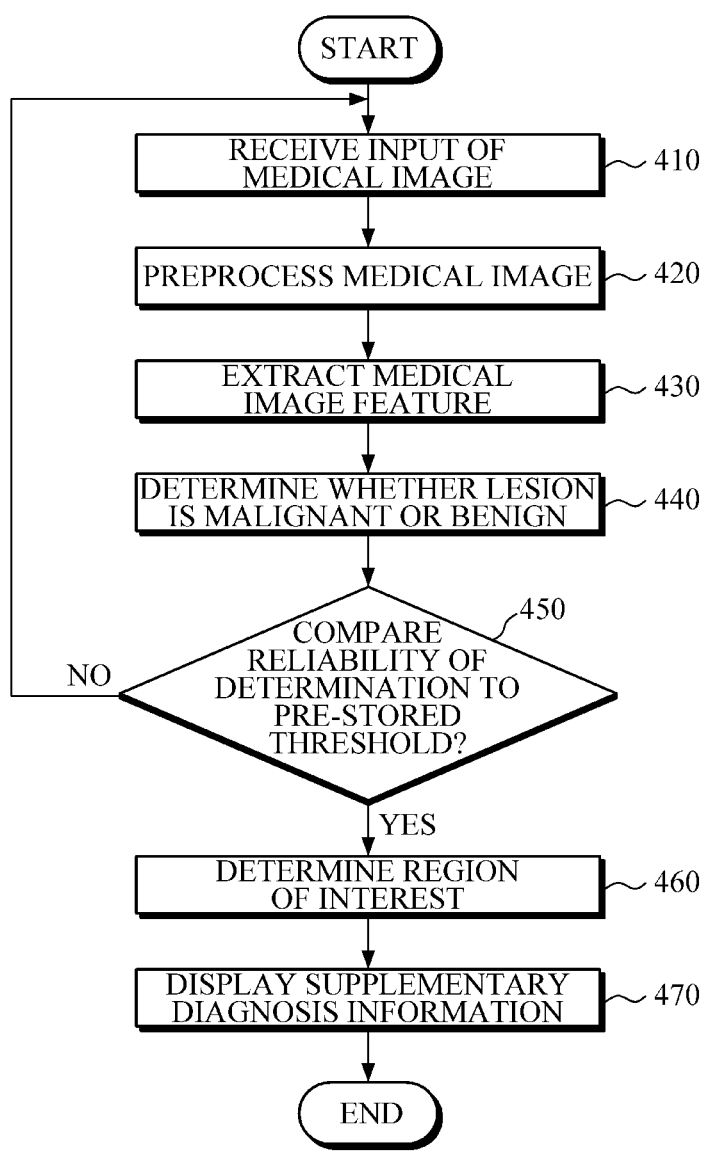
FIG. 4 is a flowchart illustrating an aspect of a method for aiding an imaging diagnosis.

FIG. 4 is a flowchart illustrating an aspect of a method for aiding an imaging diagnosis.

Referring to FIG. 4, the method of aiding imaging diagnosis includes receiving input of medical images in 410 via image input component 140, and preprocessing the input medical images in 420 to easily extract medical image features from the input medical images via preprocessor 150.

For example, the imaging diagnosis aiding apparatus 100 may preprocess medical images by normalization, channel separation, scaling, and the like of input medical images, so that medical image features may be easily extracted from medical images.

As described above, medical images may be any one of various medical images, including a Computed Radiography (CR) image, a Computed Tomography (CT) image, an ultrasonic image, a Magnetic Resonance Image (MRI), and the like.

Subsequently, medical image features are extracted from a preprocessed medical image in 430 via extractor 110. For example, the imaging diagnosis aiding apparatus 100 may process an image to detect a region suspected to have a lesion in a medical image, and may extract features of medical images by using pixel information of contours of the detected region suspected to have a lesion, regions adjacent to the contours, or regions within the contours. The features of the medical images refer to medically meaningful features that include visual pattern information of cell tissues that may be used to determine whether a lesion is benign or malignant.

Then, based on the extracted medical image features, determined determination is made whether a lesion is benign or malignant in 440 along with a reliability of determination. For example, the imaging diagnosis aiding apparatus 100 may determine whether a lesion is benign or malignant by comparing the extracted medical image features to a pre-stored diagnosis model with a reliability of determination.

Next, a reliability of determination is compared to a pre-stored threshold in 450. Upon comparison, in the case where a reliability is above a pre-stored threshold, supplementary diagnosis information is displayed in 470. For example, in the case where a reliability is above a predetermined threshold, the imaging diagnosis aiding apparatus 100 may determine whether a lesion is benign or malignant, and may display details about medical image features that lead to the determination, image locations of the medical image features, a ROI, and similar information.

The ROI is a region that includes medical image features that lead to a determination whether a region is benign or malignant, and may be configured to include regions in which a coherence of pixels is above a predetermined threshold. To this end, the method of aiding imaging diagnosis may further include determining a ROI in 460 based on the medical image features that lead to a determination whether a lesion is benign or malignant.

In an exemplary aspect, the ROI displayed in a previous medical image may be displayed in a subsequent frame image, so as to maintain the ROI.

The ROI displayed in 470 may be displayed with a dotted line in a subsequent frame image.

In the case where a reliability of determination is not above a predetermined threshold in 450, supplementary diagnosis information is not displayed, and a new medical image is input by returning to 410.

In the CAD system that analyzes a sequence of medical images in real time, supplementary diagnosis information is provided only when diagnosis results with high reliability are obtained, so as to prevent visual confusion that doctors may feel when analyzing a sequence of medical images, and to reduce a false alarm of the CAD system.

The apparatuses, units, modules, devices, and other components illustrated in FIGS. 1-4, for example, that may perform operations described herein with respect to FIGS. 1-4, for example, are implemented by hardware components. Examples of hardware components include controllers, sensors, memory, drivers, and any other electronic components known to one of ordinary skill in the art. In one example, the hardware components are implemented by one or more processing devices, or processors, or computers. A processing device, processor, or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processing device, processor, or computer includes, or is connected to, one or more memories storing instructions or software that are executed by the processing device, processor, or computer and that may control the processing device, processor, or computer to implement one or more methods described herein. Hardware components implemented by a processing device, processor, or computer execute instructions or software, such as an operating system (OS) and one or more software applications that run on the OS, to perform the operations described herein with respect to FIGS. 1-4, for example. The hardware components also access, manipulate, process, create, and store data in response to execution of the instructions or software. For simplicity, the singular term "processing device", "processor", or "computer" may be used in the description of the examples described herein, but in other examples multiple processing devices, processors, or computers are used, or a processing device, processor, or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, remote processing environments, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-4 that perform the operations described herein may be performed by a processing device, processor, or a computer as described above executing instructions or software to perform the operations described herein.

Instructions or software to control a processing device, processor, or computer to implement the hardware components and perform the methods as described above may be written as computer programs, code segments, instructions or any combination thereof, for individually or collectively instructing or configuring the processing device, processor, or computer to operate as a machine or special-purpose computer to perform the operations performed by the hardware components and the methods as described above. In one example, the instructions or software include machine code that is directly executed by the processing device, processor, or computer, such as machine code produced by a compiler. In another example, the instructions or software include higher-level code that is executed by the processing device, processor, or computer using an interpreter. Based on the disclosure herein, and after an understanding of the same, programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processing device, processor, or computer to implement the hardware components, such as discussed in any of FIGS. 1-4, and perform the methods as described above in any of FIGS. 1-4, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processing device, processor, or computer so that the processing device, processor, or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processing device, processor, or computer.

What is claimed is:

1. An imaging diagnosis aiding apparatus, comprising:
   a display;
   a memory configured to store instructions; and
   at least one processor, which upon executing the stored instructions, configured to:
      extract at least one medical image feature from a medical image,
      determine whether a lesion is malignant or benign based on the at least one extracted medical image feature,
      determine whether a reliability of a determination that the lesion is malignant or benign is above a predetermined threshold, and
      control the display to display supplementary diagnosis information and a region of interest in the medical image, in response to determining that the reliability is above the predetermined threshold,
   wherein the supplementary diagnosis information and the region of interest are not displayed in the display when the reliability is not above the predetermined threshold,
   wherein the at least one processor is further configured to:
      control the display to display the region of interest in an image frame subsequent to the medical image when the reliability is above the predetermined threshold, and
   wherein the region of interest in the image frame subsequent to the medical image is not displayed when the reliability is not above the predetermined threshold.

2. The imaging diagnosis aiding apparatus of claim 1, wherein the at least one processor is further configured to determine whether the lesion is malignant or benign based on a combination of a plurality of extracted medical image features which include the at least one medical image feature.

3. The imaging diagnosis aiding apparatus of claim 1, wherein the at least one processor is further configured to determine whether the lesion is malignant or benign by comparing the extracted at least one medical image feature with a pre-stored diagnosis model.

4. The imaging diagnosis aiding apparatus of claim 1, wherein upon determination of whether the lesion is malignant or benign, the supplementary diagnosis information further includes at least one of:
   details about medical image features that led to the determination, or an image location that includes the medical image features that led to the determination.

5. The imaging diagnosis aiding apparatus of claim 4, wherein the region of interest is a region that includes medical image features that led to the determination, and includes regions having a coherence of each pixel that is above a predetermined threshold.

6. The imaging diagnosis aiding apparatus of claim 4, wherein the at least one processor is further configured to control the display to display the region of interest in the medical image and in the image frame subsequent to the medical image.

7. The imaging diagnosis aiding apparatus of claim 6, wherein the at least one processor is further configured to control the display to display the region of interest with a dotted line in the image frame subsequent to the medical image, when the reliability of the determination is above the predetermined threshold.

8. The imaging diagnosis aiding apparatus of claim 1, wherein the medical image comprises a Computed Radiography (CR) image, a Computed Tomography (CT) image, an ultrasonic image, or a Magnetic Resonance Image (MRI).

9. The imaging diagnosis aiding apparatus of claim 1, wherein the at least one processor is further configured to preprocess the medical image by performing at least one of normalization, channel separation, or scaling.

10. A method for aiding imaging diagnosis at an imaging diagnosis aiding apparatus, the method comprising:
   extracting, by at least one processor of the imaging diagnosis aiding apparatus, at least one medical image feature from a medical image;
   determining, by the at least one processor, whether a lesion is malignant or benign based on the at least one extracted medical image feature;
   determining whether a reliability of a determination that the lesion is malignant or benign is above a predetermined threshold;
   displaying, by a display of the imaging diagnosis aiding apparatus, supplementary diagnosis information and a region of interest in the medical image, in response to determining that the reliability is above the predetermined threshold; and
   displaying, by the display, the region of interest in an image frame subsequent to the medical image when the reliability is above the predetermined threshold,
   wherein the supplementary diagnosis information is not displayed in the display when the reliability is not above the predetermined threshold, and
   wherein the region of interest in the image frame subsequent to the medical image is not display when the reliability is not above the predetermined threshold.

11. The method of claim 10, wherein the determining of whether the lesion is malignant or benign comprises determining, by the at least one processor, whether the lesion is malignant or benign based on a combination of a plurality of extracted medical image features which include the at least one medical image feature.

12. The method of claim 10, wherein the determining of whether the lesion is malignant or benign comprises determining, by the at least one processor, whether the lesion is malignant or benign by comparing the extracted at least one medical image feature with a pre-stored diagnosis model.

13. The method of claim 10, wherein upon determination whether the lesion is malignant or benign, the supplementary diagnosis information further includes at least one of:
   details about medical image features that led to the determination, or
   an image location that includes the medical image features that led to the determination.

14. The method of claim 13, wherein the region of interest is a region that includes medical image features that led to the determination, and includes regions having a coherence of each pixel that is above a predetermined threshold.

15. The method of claim 13, wherein displaying the supplementary diagnosis information comprises:

displaying, by the display, the region of interest in the medical image; and displaying, by the display, the region of interest in the image frame subsequent to the medical image.

16. The method of claim 15, wherein the displaying of the region of interest in an image frame subsequent to the medical image comprises displaying, by the display, the region of interest with a dotted line in the image frame subsequent to the medical image, when the reliability of the determination is above the predetermined threshold.

17. The method of claim 10, wherein the medical image comprises a Computed Radiography (CR) image, a Computed Tomography (CT) image, an ultrasonic image, or a Magnetic Resonance Image (MRI).

18. The method of claim 10, further comprising preprocessing, by the at least one processor, the medical image by performing at least one of normalization, channel separation, or scaling.

19. A non-transitory computer-readable medium storing one or more computer programs including instructions that, when executed by the at least one processor, cause the at least one processor to control to perform the method of claim 10.

* * * * *